US010614316B2

(12) United States Patent
Datta et al.

(10) Patent No.: US 10,614,316 B2
(45) Date of Patent: *Apr. 7, 2020

(54) ANOMALOUS EVENT RETRIEVER

(71) Applicant: International Business Machines Corporation, Armonk, NY (US)

(72) Inventors: Ankur Datta, White Plains, NY (US); Balamanohar Paluri, Atlanta, GA (US); Sharathchandra U. Pankanti, Darien, CT (US); Yun Zhai, Pound Ridge, NY (US)

(73) Assignee: International Business Machines Corporation, Armonk, NY (US)

(*) Notice: Subject to any disclaimer, the term of this patent is extended or adjusted under 35 U.S.C. 154(b) by 203 days.

This patent is subject to a terminal disclaimer.

(21) Appl. No.: 15/834,312

(22) Filed: Dec. 7, 2017

(65) Prior Publication Data

US 2018/0107881 A1   Apr. 19, 2018

Related U.S. Application Data

(63) Continuation of application No. 14/845,438, filed on Sep. 4, 2015, now Pat. No. 9,928,423, which is a
(Continued)

(51) Int. Cl.
  *G06T 7/246* (2017.01)
  *G06K 9/00* (2006.01)
  (Continued)

(52) U.S. Cl.
  CPC ....... *G06K 9/00771* (2013.01); *G06K 9/6284* (2013.01); *G06T 7/251* (2017.01); *G08B 13/19606* (2013.01); *G16B 40/00* (2019.02)

(58) Field of Classification Search
  CPC . G06T 2207/30241; G06T 7/20; G06T 7/246; G06T 7/251; G06T 7/215;
  (Continued)

(56) References Cited

U.S. PATENT DOCUMENTS

| 5,161,204 A | 11/1992 | Hutcheson et al. |
| 6,650,779 B2 | 11/2003 | Vachtesvanos et al. |

(Continued)

OTHER PUBLICATIONS

Anjum et al., Multifeature Object Trajectory Clustering for Video Analysis, Nov. 2008 [retrieved Aug. 24, 2019], IEEE Trans on Circuits and Systems for Video Tech, vol. 18, No. 11, pp. 1555-1564. Retrieved: https://ieeexplore.ieee.org/abstract/document/4633639 (Year: 2008).*

(Continued)

*Primary Examiner* — Andrew M Moyer
*Assistant Examiner* — Dennis Rosario
(74) *Attorney, Agent, or Firm* — Patrick J. Daugherty; Daugherty & Del Zopp Co., LPA

(57) ABSTRACT

Aspects determining anomalous events, wherein processors determine a trajectory of tracked movement of an object through an image field of a camera partitioned into a matrix grid of different local units. The aspects generate anomaly confidence decision values for image features extracted from video data of the tracked movement of the object as a function of fitting extracted image features to normal patterns of local motion pattern models defined by dominant distributions of extracted image features. The aspects further extract trajectory features from the video data relative to the trajectory of the tracked movement of the object, and generate global anomaly confidence decision values for the object trajectory as a function of fitting the extracted trajectory features to a normal learned motion trajectory model. The aspects determine anomalous events as a function of the generated global anomaly confidence decision value and the anomaly confidence decision values.

20 Claims, 3 Drawing Sheets

Related U.S. Application Data continuation of application No. 13/110,331, filed on May 18, 2011, now Pat. No. 9,158,976.

(51) Int. Cl.
*G08B 13/196* (2006.01)
*G16B 40/00* (2019.01)
*G06K 9/62* (2006.01)

(58) Field of Classification Search
CPC .............. G06T 7/254; G06T 7/248; G06T 2207/30232; G06T 7/277; A63B 24/0021; A63B 2024/0028; A63B 2024/0025; A63B 24/0003; G06K 9/00664; G06K 9/00771; G06K 9/3241; G06K 9/4642; G06K 9/00624; G06K 9/00335; G06K 9/00342; G06K 9/00355; G06F 3/0425; A61B 5/11; A61B 5/1114
See application file for complete search history.

(56) References Cited

U.S. PATENT DOCUMENTS

| | | | |
|---|---|---|---|
| 8,169,481 B2 | 5/2012 | Ozdemir | |
| 8,660,368 B2 * | 2/2014 | Datta | G06K 9/00778 382/103 |
| 8,744,124 B2 | 6/2014 | Venkatesh | |
| 8,855,361 B2 | 10/2014 | Millar et al. | |
| 9,158,976 B2 * | 10/2015 | Datta | G06K 9/00771 |
| 9,928,423 B2 * | 3/2018 | Datta | G06K 9/00771 |
| 2006/0045185 A1 | 3/2006 | Kiryati et al. | |
| 2008/0201116 A1 | 8/2008 | Ozdemir et al. | |
| 2009/0195401 A1 | 8/2009 | Maroney et al. | |
| 2009/0210373 A1 | 8/2009 | Yu et al. | |
| 2010/0208063 A1 | 8/2010 | Lee et al. | |

OTHER PUBLICATIONS

Jiang et al., A Dynamic Hierarchical Clustering Method for Trajectory-Based Unusual Video Event Detection, Apr. 2009 [retrieved Aug. 24, 2019], IEEE Transactions on Image Processing, vol. 18, Issue: 4,pp. 907-913. Retrieved: https://ieeexplore.ieee.org/abstract/document/4798178 (Year: 2009).*

U.S. Appl. No. 14/845,438, filed Sep. 4, 2015; Confirmation No. 8208.

Notice of Allowance (dated Nov. 14, 2017) for U.S. Appl. No. 14/845,438, filed Sep. 4, 2015, Confirmation No. 8208.

* cited by examiner

ANOMALOUS EVENT RETRIEVER

BACKGROUND

The present invention relates to the efficient ranking and selective retrieval of anomalous events (anomalies) determined in visual image data.

Determining and recognizing anomalous motion activities (anomalies) in visual image data is useful in determining occurrences or absences of certain activities or events. For example, image data of structures may be monitored for changes in expected or normal visual data patterns that are indicative of events and behaviors diverging from norms, such as immediate or potential failures of structural components or human movements or activities outside of compliance with usual safety or other activity processes and policies. If readily distinctive to human analysis, such anomalies may be identified by capturing and recording visual data through still image and video systems for subsequent or contemporaneous analysis. However, with large amounts of data, discerning anomalies of importance from other anomalies may be difficult, time consuming or inefficient, and even non-feasible. More particularly, it is not enough to merely recognize that an anomaly has occurred in the context of high frequencies or numbers anomaly occurrences, especially if some otherwise equivalent anomalies may have more importance than others.

Automated video systems and methods are known wherein computers or other programmable devices directly analyze video data and attempt to recognize anomaly objects, people, events or activities of concern, etc., through identifying anomalous motion patterns through computer vision applications. However, discernment of more significant anomalies from other anomalies or even from normal patterns, events, etc., by automated video surveillance systems and methods systems is often not reliable in realistic, real-world environments and applications due to a variety of factors. For example, visual image data may be difficult to analyze or vary over time due to clutter, poor or variable lighting and object resolutions, distracting competing visual information, etc. False alerts or missed event recognitions must also occur at an acceptable level.

BRIEF SUMMARY

In one embodiment of the present invention, a method for determining anomalous events includes determining a trajectory of tracked movement of an object through an image field of a camera that is partitioned into a matrix comprising a grid of a plurality of different local units. The method further generates anomaly confidence decision values for image features extracted from video data of the tracked movement of the object as a function of fitting the extracted image features to normal patterns of local motion pattern models that are defined by dominant distributions of the extracted image features. Said method includes extracting trajectory features from the video data relative to the trajectory of the tracked movement of the object, and generating a global anomaly confidence decision value for the object trajectory as a function of fitting the extracted trajectory features to a normal learned motion trajectory model, wherein the global anomaly confidence decision value indicates a likelihood that the object trajectory is normal or anomalous. Thus, the method determines whether the tracked movement of the object includes an anomalous event as a function of the generated global anomaly confidence decision value and the anomaly confidence decision values.

In another embodiment, a system has a processing unit, computer readable memory and a computer readable storage medium device with program instructions that cause the processing unit to determine a trajectory of tracked movement of an object through an image field of a camera that is partitioned into a matrix comprising a grid of a plurality of different local units. The processing unit further generates anomaly confidence decision values for image features extracted from video data of the tracked movement of the object as a function of fitting the extracted image features to normal patterns of local motion pattern models that are defined by dominant distributions of the extracted image features. Said processing unit includes extracting trajectory features from the video data relative to the trajectory of the tracked movement of the object, and generates a global anomaly confidence decision value for the object trajectory as a function of fitting the extracted trajectory features to a normal learned motion trajectory model, wherein the global anomaly confidence decision value indicates a likelihood that the object trajectory is normal or anomalous. Thus, the processing unit determines whether the tracked movement of the object includes an anomalous event as a function of the generated global anomaly confidence decision value and the anomaly confidence decision values.

In another embodiment, an article of manufacture has a computer readable storage medium device with computer readable program code embodied therewith, the computer readable program code comprising instructions that, when executed by a computer processor, cause the computer processor to determine a trajectory of tracked movement of an object through an image field of a camera that is partitioned into a matrix comprising a grid of a plurality of different local units. The processor is further caused to generate anomaly confidence decision values for image features extracted from video data of the tracked movement of the object as a function of fitting the extracted image features to normal patterns of local motion pattern models that are defined by dominant distributions of the extracted image features. The processor is further caused to extract trajectory features from the video data relative to the trajectory of the tracked movement of the object, and generate a global anomaly confidence decision value for the object trajectory as a function of fitting the extracted trajectory features to a normal learned motion trajectory model, wherein the global anomaly confidence decision value indicates a likelihood that the object trajectory is normal or anomalous. Thus, the processor is caused to determine whether the tracked movement of the object includes an anomalous event as a function of the generated global anomaly confidence decision value and the anomaly confidence decision values.

BRIEF DESCRIPTION OF THE SEVERAL VIEWS OF THE DRAWINGS

These and other features of this invention will be more readily understood from the following detailed description of the various aspects of the invention taken in conjunction with the accompanying drawings in which.

Figure 1:
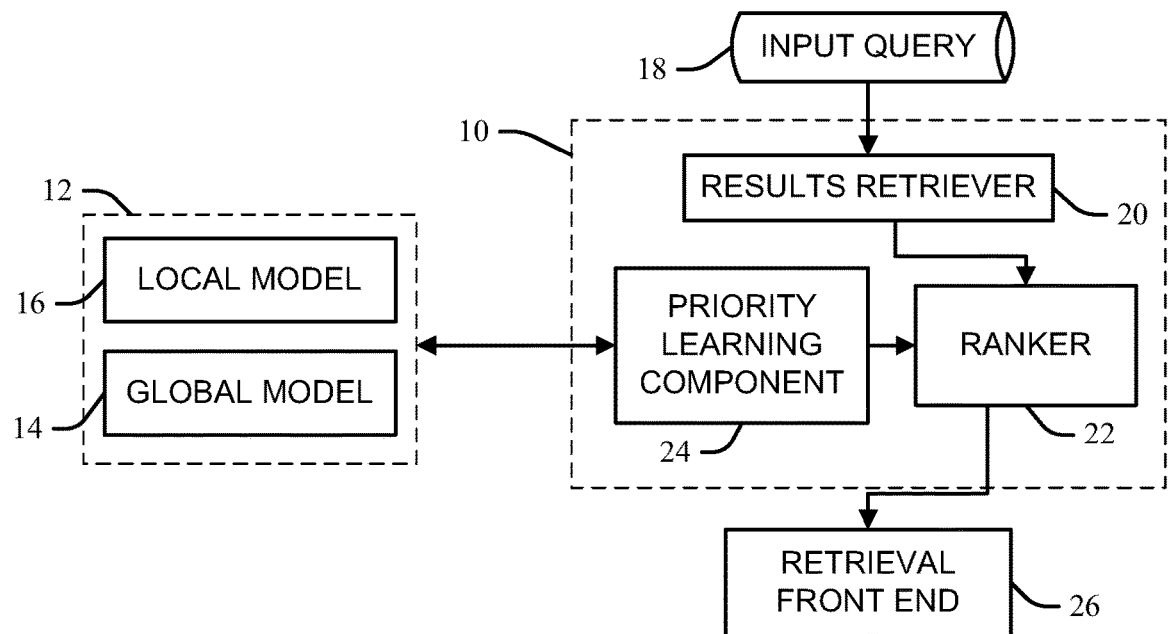
FIG. 1 is a diagrammatic flow chart illustration of an embodiment of an article or system that uses models learned from an anomaly detector to rank detected anomalies according to the present invention.

The drawings are not necessarily to scale. The drawings are merely schematic representations, not intended to portray specific parameters of the invention. The drawings are intended to depict only typical embodiments of the invention and, therefore, should not be considered as limiting the scope of the invention. In the drawings, like numbering represents like elements.

DETAILED DESCRIPTION

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in a baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

FIG. 1 is a diagrammatic illustration of one embodiment of an anomaly retriever or system 10 (for example, a programmable device, computer system, etc.) according to the present invention that uses models learned from anomaly detection to rank detected anomalies. In response to an input query 18 for one or more anomalies, a Results Retriever 20 retrieves a plurality of anomaly results provided through use of an associated Anomaly Detection system or component 12, which in the present example has both a Local Model 16 and a Global Model 14, though other embodiments may use more or less, or only one, of the Local Model 16 and the Global Model 14, or use different anomaly detection models.

The anomaly results retrieved from anomaly detection at 12 are ranked (or prioritized) by a Ranker 22 as a function of weightings learned by an online Priority Learning Component 24, which learns the weightings through clustering features extracted by the Anomaly Detector 12 and further determines importance and relevance parameters with respect to associated local areas of the field of image of the video data in view of learned models of the Anomaly Detector 12. The retrieved results are presented as a function of their ranking by the Ranker 22 to a user submitting the query 18 in a Retrieval Front End 26, for example in a browser or other user interface.

Figure 2:
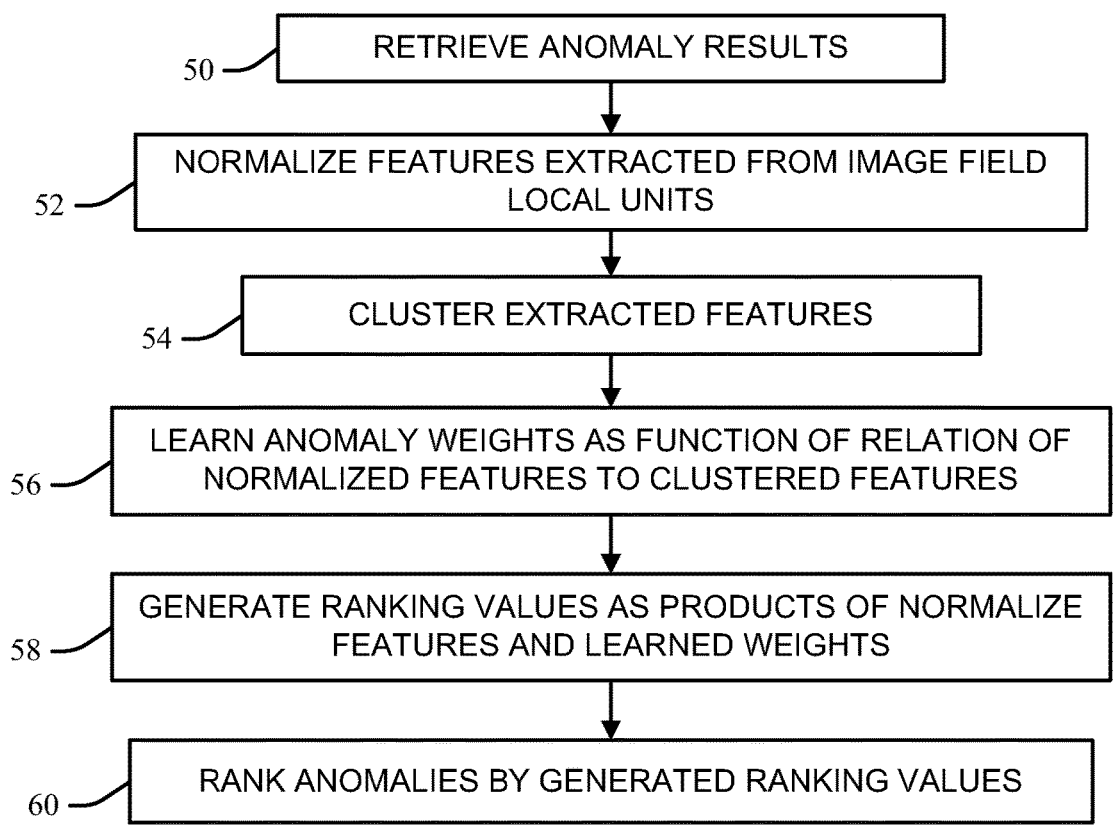
FIG. 2 is a diagrammatic flow chart illustration of an embodiment of a method or system for priority learning and ranking of detected anomalies according to the present invention.

FIG. 2 is a diagrammatic flow chart illustration of one embodiment of a method or system for priority learning and ranking of detected anomalies according to the present invention. Thus, at 50 a plurality of anomaly results are retrieved from an anomaly detection module comprising a plurality of local models in response to an input query for an anomaly. The anomaly detection module local models comprise image feature values extracted from an image field of video image data with respect to each of a plurality of different predefined spatial and temporal local units, and each of the plurality of anomaly results are determined by respective failures to fit to applied ones of the anomaly detection module local models.

At 52 image features extracted from the image field local units that are associated with each of the plurality of anomaly results are normalized. At 54 image feature values extracted from the each image field local units that are associated with the each of the plurality of anomaly results are clustered. At 56 weights for each of the anomaly results are learned as a function of a relation of their normalized extracted image feature values to the clustered image feature values. At 58 the anomaly normalized extracted feature values are multiplied by their respective learned weights to generate respective ranking values, and the anomalies and thus ranked by their respective generated ranking values at 60.

Figure 3:
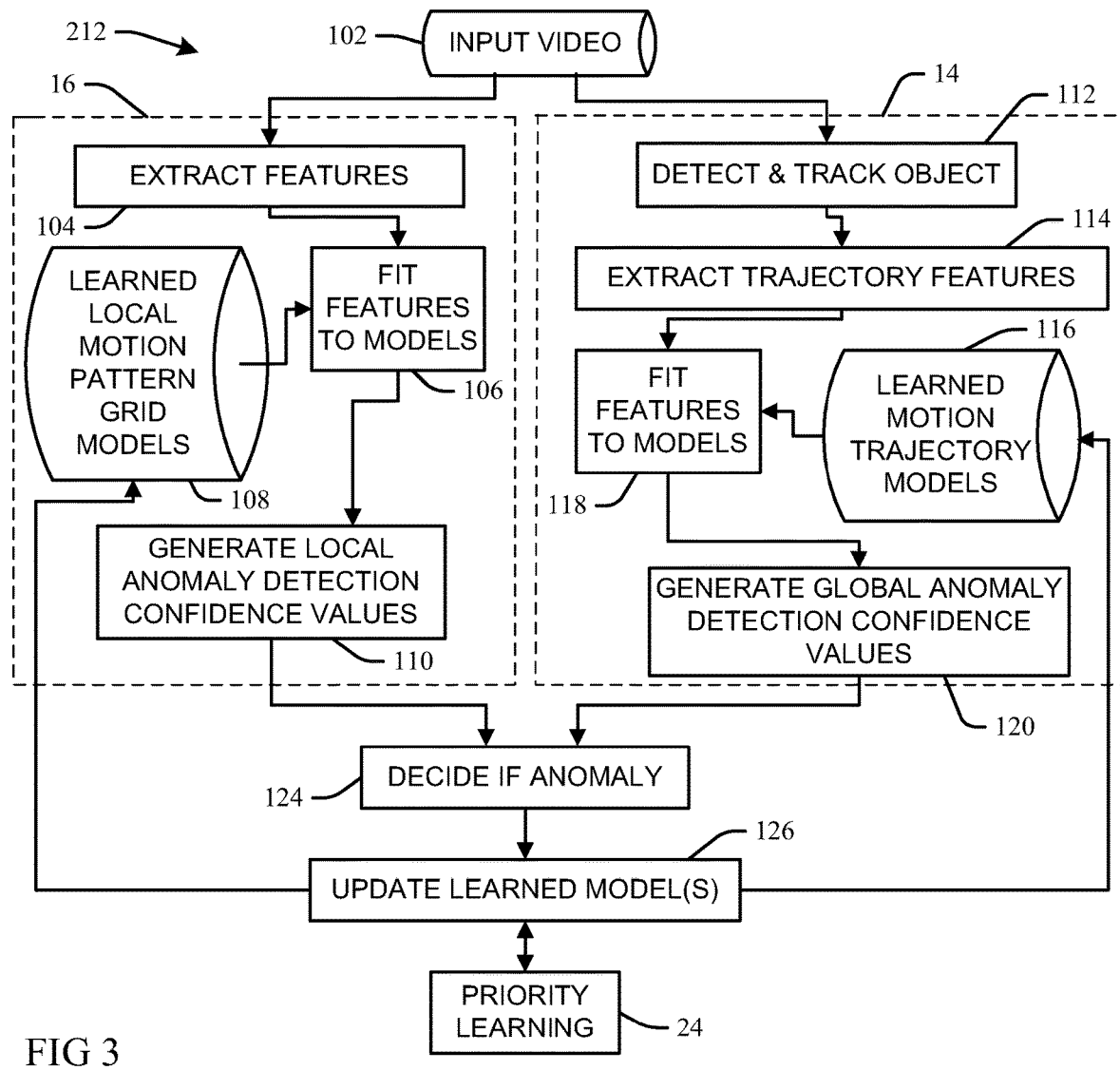
FIG. 3 is a diagrammatic flow chart illustration of an anomaly detection module or process according to embodiments of the present invention.

FIG. 3 is a diagrammatic illustration of one embodiment of a local model/global model detector structure 212 appropriate for performing the anomaly detection at 12 of FIG. 1. In the local anomaly detection model 14 an image field of a video data input 102 is partitioned into a plurality of different predefined spatial and temporal local areas or units, wherein at 104 a local detector extracts and clusters image features with respect to each unit. Embodiments of the present invention do not require prior knowledge of either normal or abnormal patterns, but instead they may automatically learn normal patterns by learning dominant behaviors from the extracted and clustered features.

Various extracted video features appropriate for use in embodiments of the present invention include, but are not limited to, color, motion, texture, edges, etc., and may be extracted from each local unit and further refined by a dimension reduction technique. Dominant distributions of the extracted features are found and used to define "normal" patterns, wherein rare patterns define "anomaly" or "abnormal" patterns. Learned models are constructed by building either parametric models (for example, Gaussian) or non-parametric models (for example, kernel density estimation) for the learned feature distributions. Extracted local unit local image features may be fit to the models 108 to "learn" revisions, for example to align to clustered similarities of new extracted features.

At 106 the image features extracted by a local detector for each local unit are compared to learned local motion pattern models 108 for each local unit to generate local anomaly detection confidence decision values at 110 for each of said local units, more particularly whether the features extracted relevant to object motion within input video data indicate that the object motion within each particular local unit is either normal or expected, or instead anomalous (abnormal or unexpected), in view of the learned model patterns for the local units. Local global anomaly detection confidence decision values 110 may be binary normal or anomaly values (i.e. "yes" or "no", or "one" or "zero"), or they be graduated values or other non-binary values. Thus, anomaly detection decisions are made at 110 based on individual grid fitting confidences, and an anomaly decision may be made for each local unit. Each local unit may be assigned a label, with the distribution of the labels giving information content of the local unit. Internal appearance patterns (for example, entropy) may be used as a measure to find the significance metric of each such local unit, which may be embedded in the anomaly detection models 14/16 to improve them, and also used to prioritize the anomalies by revising weightings used in ranking at 22.

In the global anomaly detection module 14, at 112 the presence of an object in an image field of the video data input 102 is detected and its movement tracked through the image field over time through a trajectory of motion, for example through background modeling and subtraction processes, though other techniques may be practiced. Illustrative but not exhaustive tracked movement examples include a person object moving relative to (for example, travelling up) a staircase object and turning down a hallway object, and observing a changing separation value between two structural elements in an assembly over time that may be indicative of a structural change of the assembly or elements. At 114 a global feature extractor extracts image features from the video data relative to the trajectory of the object tracked through the image field with respect to all or a portion of the image field. At 118 a global anomaly detector compares the extracted trajectory features to a learned motion trajectory model 116 to generate a global anomaly detection confidence decision values 120 for the object trajectory: for example, whether the trajectory fits to a normal learned trajectory, or not. The decision value at 120 provides an objective measure of likelihood that the object trajectory is either normal or instead anomalous.

At 124 the system or process decides whether or not an anomaly has occurred as a function of the individual local unit local anomaly detection confidence decision values 110 and the global anomaly detection confidence values 120. The decision at 124 may be based on the individual local and global anomaly detection confidence values 110/120, or through a combination or fusion of the respective values 110/120, for example fusing the values 110 for each of the grids that an object passes through in a trajectory with the global value 120 for the trajectory to provide a fused value.

Figure 4:
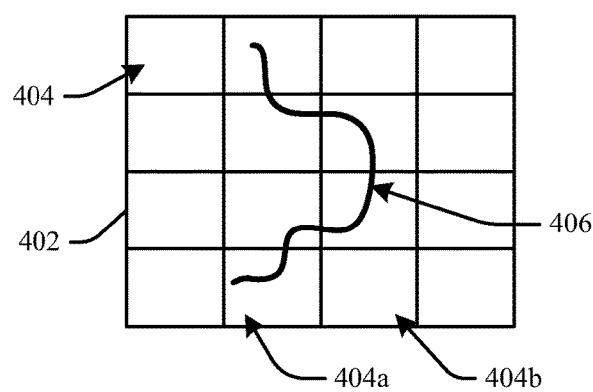
FIG. 4 is a graphic illustration of a partitioned video data image field according to embodiments of the present invention.

FIG. 4 illustrates an example of an image field 402 of input video data 102 which comprises images of objects that describe a trajectory of motion 406 over time (for example, a person travelling along a concourse within the image field 402). The image field 402 is divided into a matrix of predefined spatial and temporal local units or grids 404. The object trajectory 406 travels through some of the grids 404*a*, but does not enter into other grids 404*b*. In one embodiment, the local anomaly detection confidence values 110 of the grids 404*a* that include the tracked trajectory 406 are combined or fused with the global anomaly detection confidence value 120 of the tracked trajectory 406 to decide at 124 if the object movement is normal or an anomaly. A total number of the image field grids 404*a* that include the object trajectory may be less than a totality of all of the partition grids 404 (inclusive of said grids 404a and the other grids 404b), leading to efficiencies over other systems that may extract features for every one of the grids 404.

At 126 the anomaly detection module 212 updates or refines, or builds new models, for the local and/or global learned models 108 and/or 116 as a function of the anomaly decisions at 124 through analyzing activity patterns from the video image data input 102, and/or through feedback or other data from the priority learning at 24 of the anomaly retriever 10. Analysis at 126 may be carried on in different scales, both in the local and global levels of the video, and in both spatial and temporal domains.

Rankings are accomplished at 22 using a variety of context measures, and as a function of clustering of extracted feature values (in some embodiments, as a function of comparing the clusters with the learned local model 108 local units), and of weightings learned by the priority learning at 24. Various ranking or weighting mechanisms may be used to compute final ranking scores through considering and combining the various features. In one embodiment, a linear weighted sum is used, wherein all the extracted features ($F_i$) are normalized to have feature values between zero and one, and weights ($W_i$) provided by the priority learning at 24 are chosen pursuant to equation [1]:

$$\sum_i W_i = 1. \quad [1]$$

For each detected anomaly a relevance measure ranking is computed using formulation [2]:

$$\sum_i W_i * F_i; \quad [2]$$

wherein the retrieved results are displayed at 26 (FIG. 1) in the order of relevance measure.

Embodiments of the present invention provide for online priority learning at 24 to learn the weights ($W_i$) from features captured from the underlying activity that may include subjective information. Some embodiments use a linear weighted function based on feedback from anomaly detection processes or components or from user inputs to "learn" updates to the weights ($W_i$), thus to make them better over time. Extracted clusters and the cluster scores carry salient information about the underlying activity and how aberrant it is to other activities. In one aspect, embodiments that divide anomaly detection into separate local and global processes allow for the categorization of anomalies in a better manner over conventional anomaly detection methods, through enabling the imposition of spatial, temporal and spatio-temporal constraints to learn the weights ($W_i$) used to rank the results.

For example, the weights ($W_i$) may be revised through priority learning by determining a spatial location of a retrieved anomaly within the field of view of the input video data as correlated to features of interest of the real-world scene represented within the field of view and assign a ranking weighting accordingly. Thus, a first cluster-outlier anomaly may receive a higher weight ($W_i$) to achieve a higher ranking (or ranking metric value) if its spatial location is within a portion of the field of view of the input video that is correlated with a cordoned off area of the real-world scene represented within the field of view (for example, the rails of a train within a passenger station), as compared with the weight ($W_i$) assigned to another second anomaly that is also a cluster outlier (perhaps having an equivalent distance to a center of a same cluster of object motion events) but is spatially outside the portion (and thus not in the rail area). Object activity within this portion area is thus predetermined to be more concerning than anomaly activity outside of it.

The weights may also be a function of distance to centers of clustered events, or of clusters of other anomalies. Thus, anomalies occurring within an image field outside of a cluster and farther from the cluster center area of the image may be ranked proportionally higher than those that are closer when the context of the object activity indicates that the greater spatial distance occurrences are more concerning; in one example, the greater distance may suggest that a detected person object has removed himself from the sight of others in order to engage in an illicit activity. Accordingly, anomalies which are more distant ($C_i$) from centers of clusters of the extracted features may also be given higher weights ($W_i$) compared to the ones closer according to formulation [3]:

$$W_i = |C_i - F_i|^2. \quad [3]$$

Or, in the converse, anomalies occurring within an image field outside of a cluster and closer to the cluster center area of the image may be weighted proportionally higher (hence, to be ranked higher) than those that are both outside of the cluster and farther from the cluster center.

The distribution of a plurality of feature clusters may also be used to infer how frequently anomalies occur and thus to assign respective weights ($W_i$). Temporal data such as duration or time of day may also be used to rank or weight anomalies. For example, anomalies at night may be more concerning than daytime activities (which are more likely to be normal or non-concealed activities). Activities of longer duration may be ranked or weighted higher: a longer running time in a station area may indicate a fleeing activity, rather a short run to catch a train.

Frequency of anomaly occurrence may also be used to rank or weight. Thus, a rarely occurring anomaly (for example, movement in a subset area of a restricted area that is rarely occupied), or a frequently occurring anomaly (for example, one that is more strongly correlated with an activity of concern than another anomaly) may merit enhanced attention.

Weights may also reflect camera priority. Thus, each of a plurality of different cameras may have different weights representative of priorities assigned to associated data. In one embodiment, with regard to reporting an anomaly of a running person, a camera facing subway tracks is ranked higher than a camera facing a turnstile area. A type of the anomaly may also merit different rankings/weightings based on its context: placing a large bag in a refuse receptacle may not be concerning with respect to a building dumpster, but in a public trash can in an assembly area, where occupants are not expected to have large bags of rubbish to dispose of, would be ranked/weighted higher.

In prior art large video data implementations with large pluralities of cameras, anomaly detection is generally performed with respect to individual camera data without communication between cameras. In contrast, embodiments of the present invention enable a user to select a region or subset set of cameras through the front-end retrieval interface 26 for anomaly retrieval and ranking to across the selected cameras, and wherein the priority learning component or process may increase weightings (and thus rankings)

of anomalies across the multiple selected cameras. For example, where one anomaly near a secure zone is considered more important than tens of anomalies in another area, priority learning may automatically adjust the rankings of such anomalies upward. In one embodiment, the weights ($W_i$) assigned to anomalies from a given camera are determined as a function of a prior importance value ($PI_i$) given to the camera based on the type of anomalies that can be expected to occur, multiplied by an updated importance value ($UI_i$) for the camera based on the type of anomalies and number of anomalies that are observed to occur in the camera by anomaly detection, the priority learning thus continually updating the assigned weight ($W_i$) in an ongoing learning process in proportion to its initial importance.

A variety of methods and processes may be used for feature detection and extraction according to embodiments of the present invention. In one embodiment, feature vectors comprising ten dimensions are utilized within the local and global models 14/16, eight for directional components and two for velocity in horizontal and vertical directions, wherein spatiotemporal feature vectors are derived therefrom (for example, by concatenating the directional vectors over a number of video image frames); wherein Matlab™ or Principal Component Analysis (PCA) is used to reduce dimensionality; and agglomerative clustering of the feature vectors is used (which in one aspect helps in providing a hierarchy). MATLAB is a trademark of The MathWorks, Inc., in the United States or other countries.

Thus, embodiments of the present invention learn the significance of events that are spatial and temporal in nature and use the learned significance measure(s) to rank or prioritize retrieved anomalies to provide more efficient anomaly detection. Information theory techniques (for example, Entropy, Kolomogorov property, etc.) may be used to extract significance measure metrics (such as the relevance score ($R_i$) discussed above) for each local unit, gird or other field of view partition. In one aspect, such significance measurement metrics essentially magnify the anomalies retrieved with respect to local units where the probability of an anomaly occurring is high, and subdue the anomalies retrieved with respect to the other local units through lowered rankings, and wherein the significance measure(s) may be updated online instead of during other, offline training.

Standard prior art metrics for analyzing and prioritizing anomalies such as mean, median, frequency will not provide comparable rankings as they are not responsive to, nor do they capture, the underlying activity. In contrast, embodiments of the present invention that use local and global learned models enable better ranking of the anomalies, as the underlying anomaly clusters and their distribution contain valuable information that is incorporated into prioritizing results for better retrieval. By using global trajectories and local motion patterns, certain type of anomalies may be prioritized over others according to the needs of the end user.

Figure 5:
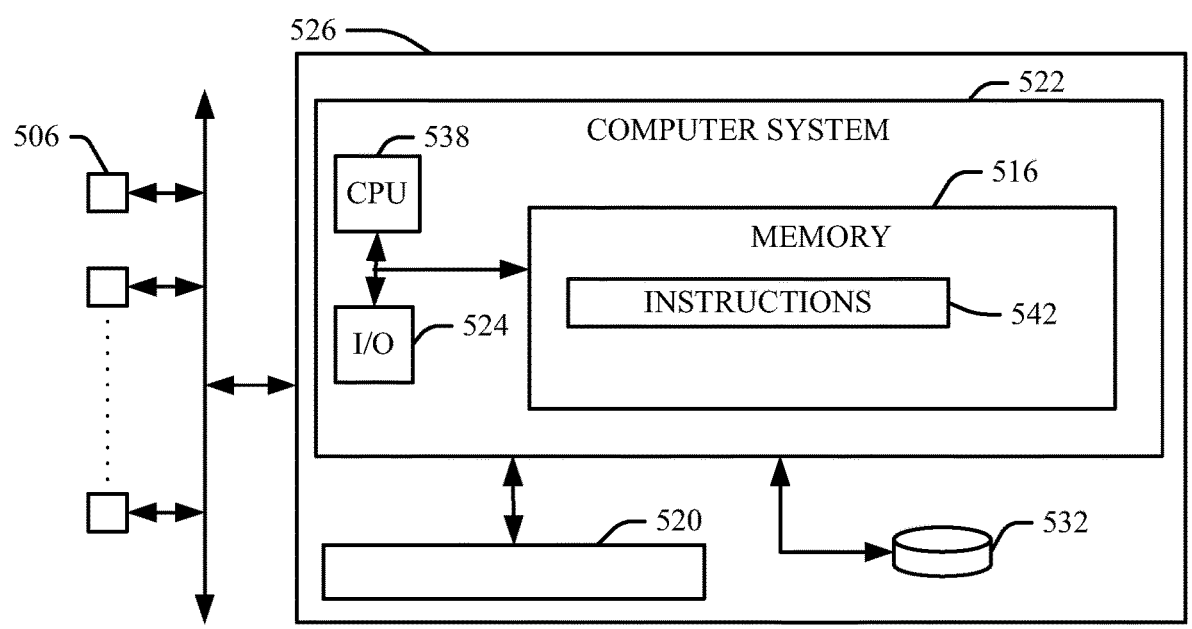
FIG. 5 is a block diagram illustration of a computerized implementation of an embodiment of the present invention.

Referring now to FIG. 5, an exemplary computerized implementation of an embodiment of the present invention includes computer or other programmable device 522 in communication with other devices 506 (for example, a video camera or video server, or a memory device comprising a database of images, etc.) that uses models learned from anomaly detection to rank detected anomalies as described above with respect to FIGS. 1 through 4, for example in response to instructions 542 within computer readable code residing in a computer memory 516, or in the storage system 532, another device 506 or other computer readable storage medium that is accessed through a computer network infrastructure 526. Thus, the instructions, when implemented in a processing unit (CPU) 538 may provide anomaly detection through combining outputs from local and global modules as described above with respect to FIGS. 1-4.

The computer 522 comprises various components, some of which are illustrated within the computer 522. More particularly, as shown, the computer 522 includes a processing unit (CPU) 538 in communication with one or more external I/O devices/resources 524, storage systems 532 or other devices 520. Moreover, the processing unit 538 may comprise a single processing unit, or be distributed across one or more processing units in one or more locations, e.g., on a client and server. Similarly, the memory 516 and/or the storage system 532 can comprise any combination of various types of data storage and/or transmission media that reside at one or more physical locations. Further, I/O interfaces 524 can comprise any system for exchanging information with one or more of an external server and/or client (not shown). Still further, it is understood that one or more additional components (e.g., system software, math co-processing unit, etc.), not shown, can be included in the computer 522.

Embodiments of the present invention may also perform process steps of the invention on a subscription, advertising, and/or fee basis. That is, a service provider could offer to use models learned from anomaly detection to rank detected anomalies as described above with respect to FIGS. 1-5. Thus, the service provider can create, maintain, and support, etc., a computer infrastructure, such as the network computer system 522, or network environment 526 (or parts thereof) that perform the process steps of the invention for one or more customers. In return, the service provider can receive payment from the customer(s) under a subscription and/or fee agreement and/or the service provider can receive payment from the sale of advertising content to one or more third parties. Services may comprise one or more of: (1) installing program code on a computing device, such as the computers/devices 522, from a computer-readable medium device 516, 520 or 506; (2) adding one or more computing devices to a computer infrastructure; and (3) incorporating and/or modifying one or more existing systems of the computer infrastructure to enable the computer infrastructure to perform the process steps of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof. Certain examples and elements described in the present specification, including in the claims and as illustrated in the Figures, may be distinguished or otherwise identified from others by unique adjectives (e.g. a "first" element distinguished from another "second" or "third" of a plurality of elements, a "primary" distinguished from a "secondary" one or "another" item, etc.) Such identifying adjectives are generally used to reduce confusion or uncertainty, and are not to be construed to limit the claims to any specific illustrated element or embodiment, or to imply any precedence, ordering or ranking of any claim elements, limitations or process steps.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method for determining anomalous events, the method comprising executing on a processor:
    determining a trajectory of tracked movement of an object through an image field of a camera that is partitioned into a matrix comprising a grid of a plurality of different local units;
    generating a plurality of anomaly confidence decision values for image features extracted from video data of the tracked movement of the object as a function of fitting the extracted image features to normal patterns of a plurality of local motion pattern models that are defined by dominant distributions of the extracted image features;
    extracting trajectory features from the video data relative to the trajectory of the tracked movement of the object;
    generating a global anomaly confidence decision value for the object trajectory as a function of fitting the extracted trajectory features to a normal learned motion trajectory model, wherein the global anomaly confidence decision value indicates a likelihood that the object trajectory is normal or anomalous; and
    determining whether the tracked movement of the object comprises an anomalous event as a function of the generated global anomaly confidence decision value and the anomaly confidence decision values.

2. The method of claim 1, wherein the trajectory data comprises tracking motion of the object that passes through a subset of the local units that is less than a totality of the plurality of the different local units, the method comprising extracting image features from the video data with respect to only each of the subset of the local units of the plurality of local units.

3. The method of claim 1, further comprising:
    integrating computer-readable program code into a computer system comprising the processor, a computer readable memory in circuit communication with the processor, and a computer readable storage medium in circuit communication with the processor; and
    wherein the processor executes program code instructions stored on the computer-readable storage medium via the computer readable memory and thereby performs the determining the trajectory of the tracked movement of the object, the generating the plurality of anomaly confidence decision values for the extracted image features, the extracting the trajectory features, the generating the global anomaly confidence decision value, and the determining whether the tracked movement of the object comprises an anomalous event.

4. The method of claim 1, wherein the generating the plurality of anomaly confidence decision values is further a function of fitting the extracted image features to anomaly patterns of the plurality of local motion pattern models that are defined by rare distributions of the extracted image features.

5. The method of claim 4, further comprising:
    learning the normal patterns and the anomaly patterns of the plurality of local motion pattern models, one for each of the subset of the local units, wherein the normal patterns are defined by finding dominant distributions of the extracted image features within respective ones of the subset of the local units, and the anomaly patterns are defined by rare distributions of the extracted image features within the respective ones of the subset of the local units;
    generating the plurality of anomaly confidence decision values as a function of fitting the image features extracted for each of the subset of the local units from the video data input of the tracked object to the plurality of the learned local motion pattern models of the respective subset of the local units by determining whether the features extracted relevant to the object's motion within the video data indicate that the object's motion within each particular local unit is one of said normal patterns or anomaly patterns in view of the plurality of the learned local motion pattern models for the local units; and
    clustering the image feature values extracted from the image field's subset of the local units that are associated with the each of the plurality of anomaly confidence decision values.

6. The method of claim 1, further comprising:
    clustering extracted image feature values associated with each of the plurality of anomaly confidence decision values;
    determining spatial locations within a field of view of the camera of the clustered extracted image feature values of the anomaly confidence decision values that are correlated to features of interest of a real-world scene represented within the field of view; and
    assigning weightings to each of the plurality of anomaly confidence decision values as a function of spatial relation of the spatial locations of the clustered extracted image feature values of the anomaly confidence decision values to a portion of the field of view of that is correlated with a cordoned off area of the real-world scene.

7. The method of claim 6, further comprising:
    ranking the plurality of anomaly confidence decision values as a function of their respective assigned weightings; and
    prioritizing anomaly event determinations as a function of the ranking of the anomaly confidence decision values.

8. The method of claim 7, wherein the ranking the plurality of anomaly confidence decision values as a function of their respective assigned weightings comprises:
    multiplying normalized values of the extracted features of the anomaly confidence decision values of the subset of the local units by their respective learned weights to generate respective ranking values; and
    ranking the plurality of anomaly confidence decision values by their generated respective ranking values.

9. A system, comprising:
    a processor;
    computer readable memory in circuit communication with the processor; and a computer readable storage medium in circuit communication with the processor and the computer readable memory; and wherein the processor executes program instructions stored on the computer-readable storage medium via the computer readable memory and thereby:

determines a trajectory of tracked movement of an object through an image field of a camera that is partitioned into a matrix comprising a grid of a plurality of different local units;

generates a plurality of anomaly confidence decision values for image features extracted from video data of the tracked movement of the object as a function of fitting the extracted image features to normal patterns of a plurality of local motion pattern models that are defined by dominant distributions of the extracted image features;

extracts trajectory features from the video data relative to the trajectory of the tracked movement of the object;

generates a global anomaly confidence decision value for the object trajectory as a function of fitting the extracted trajectory features to a normal learned motion trajectory model, wherein the global anomaly confidence decision value indicates a likelihood that the object trajectory is normal or anomalous; and determines whether the tracked movement of the object comprises an anomalous event as a function of the generated global anomaly confidence decision value and the anomaly confidence decision values.

10. The system of claim 9, wherein the trajectory data comprises tracking motion of the object that passes through a subset of the local units that is less than a totality of the plurality of the different local units; and wherein the processor executes the program instructions stored on the computer-readable storage medium via the computer readable memory and thereby extracts image features from the video data with respect to only each of the subset of the local units of the plurality of local units.

11. The system of claim 9, wherein the processor executes the program instructions stored on the computer-readable storage medium via the computer readable memory and thereby generates the plurality of anomaly confidence decision values as a function of fitting the extracted image features to anomaly patterns of the plurality of local motion pattern models that are defined by rare distributions of the extracted image features.

12. The system of claim 11, wherein the processor executes the program instructions stored on the computer-readable storage medium via the computer readable memory and thereby:

learns the normal patterns and the anomaly patterns of the plurality of local motion pattern models, one for each of the subset of the local units, wherein the normal patterns are defined by finding dominant distributions of the extracted image features within respective ones of the subset of the local units, and the anomaly patterns are defined by rare distributions of the extracted image features within the respective ones of the subset of the local units;

generates the plurality of anomaly confidence decision values as a function of fitting the image features extracted for each of the subset of the local units from the video data input of the tracked object to the plurality of the learned local motion pattern models of the respective subset of the local units by determining whether the features extracted relevant to the object's motion within the video data indicate that the object's motion within each particular local unit is one of said normal patterns or anomaly patterns in view of the plurality of the learned local motion pattern models for the local units; and clusters the image feature values extracted from the subset of the local units that are associated with the each of the plurality of anomaly confidence decision values.

13. The system of claim 9, wherein the processor executes the program instructions stored on the computer-readable storage medium via the computer readable memory and thereby:

clusters extracted image feature values associated with each of the plurality of anomaly confidence decision values;

determines spatial locations within a field of view of the camera of the clustered extracted image feature values of the anomaly confidence decision values that are correlated to features of interest of a real-world scene represented within the field of view; and assigns weightings to each of the plurality of anomaly confidence decision values as a function of spatial relation of the spatial locations of the clustered extracted image feature values of the anomaly confidence decision values to a portion of the field of view of that is correlated with a cordoned off area of the real-world scene.

14. The system of claim 13, wherein the processor executes the program instructions stored on the computer-readable storage medium via the computer readable memory and thereby:

ranks the plurality of anomaly confidence decision values as a function of their respective assigned weightings; and prioritizes anomaly event determinations as a function of the ranking of the anomaly confidence decision values.

15. The system of claim 14, wherein the processor executes the program instructions stored on the computer-readable storage medium via the computer readable memory and thereby ranks the plurality of anomaly confidence decision values as a function of their respective assigned weightings by:

multiplying normalized values of the extracted features of the anomaly confidence decision values of the subset of the local units by their respective learned weights to generate respective ranking values; and ranking the plurality of anomaly confidence decision values by their generated respective ranking values.

16. A computer program product for determining anomalous events, comprising:

a computer readable hardware storage medium device having computer readable program code embodied therewith, the computer readable program code comprising instructions for execution by a computer processor that cause the computer processor to:

determine a trajectory of tracked movement of an object through an image field of a camera that is partitioned into a matrix comprising a grid of a plurality of different local units;

generate a plurality of anomaly confidence decision values for image features extracted from video data of the tracked movement of the object as a function of fitting the extracted image features to normal patterns of a plurality of local motion pattern models that are defined by dominant distributions of the extracted image features;

extract trajectory features from the video data relative to the trajectory of the tracked movement of the object;

generate a global anomaly confidence decision value for the object trajectory as a function of fitting the extracted trajectory features to a normal learned motion trajectory model, wherein the global anomaly confidence decision value indicates a likelihood that the object trajectory is normal or anomalous; and determine whether the tracked movement of the object comprises an anomalous event as a function of the generated global anomaly confidence decision value and the anomaly confidence decision values.

17. The computer program product of claim 16, wherein the computer readable program code instructions for execution by the computer processor, further cause the computer processor to:

generate the plurality of anomaly confidence decision values as a function of fitting the extracted image features to anomaly patterns of the plurality of local motion pattern models that are defined by rare distributions of the extracted image features.

18. The computer program product of claim 17, wherein the normalized values of the extracted features of the anomaly confidence decision values of each of the subset of the local units of the first and the second anomaly confidence decision values are outliers from and have the same distance to a center of a cluster of extracted features of a one of the learned motion pattern local models.

19. The computer program product of claim 18, wherein the computer readable program code instructions for execution by the computer processor, further cause the computer processor to:

learn the normal patterns and the anomaly patterns of the plurality of local motion pattern models, one for each of the subset of the local units, wherein the normal patterns are defined by finding dominant distributions of the extracted image features within respective ones of the subset of the local units, and the anomaly patterns are defined by rare distributions of the extracted image features within the respective ones of the subset of the local units;

generate the plurality of anomaly confidence decision values as a function of fitting the image features extracted for each of the subset of the local units from the video data input of the tracked object to the plurality of the learned local motion pattern models of the respective subset of the local units by determining whether the features extracted relevant to the object's motion within the video data indicate that the object's motion within each particular local unit is one of said normal patterns or anomaly patterns in view of the plurality of the learned local motion pattern models for the local units; and cluster the image feature values extracted from the subset of the local units that are associated with the each of the plurality of anomaly confidence decision values.

20. The computer program product of claim 18, wherein the computer readable program code instructions for execution by the computer processor, further cause the computer processor to cluster extracted image feature values associated with each of the plurality of anomaly confidence decision values;

determine spatial locations within a field of view of the camera of the clustered extracted image feature values of the anomaly confidence decision values that are correlated to features of interest of a real-world scene represented within the field of view;

assign weightings to each of the plurality of anomaly confidence decision values as a function of spatial relation of the spatial locations of the clustered extracted image feature values of the anomaly confidence decision values to a portion of the field of view of that is correlated with a cordoned off area of the real-world scene;

rank the plurality of anomaly confidence decision values as a function of their respective assigned weightings; and prioritize anomaly event determinations as a function of the ranking of the anomaly confidence decision values.

* * * * *